United States Patent [19]

Upsher

[11] Patent Number: 4,527,553
[45] Date of Patent: Jul. 9, 1985

[54] LARYNGOSCOPE WITH IMPROVED LIGHT SOURCE

[76] Inventor: Michael S. Upsher, 2957 Adeline Dr., Burlingame, Calif. 94010

[21] Appl. No.: 144,704

[22] Filed: Apr. 28, 1980

[51] Int. Cl.³ .............................................. A61B 1/26
[52] U.S. Cl. ........................................ 128/11; 128/16
[58] Field of Search ............................... 128/11, 6, 16

[56] References Cited

U.S. PATENT DOCUMENTS

| | | | |
|---|---|---|---|
| 1,247,346 | 11/1917 | Stern | 128/16 |
| 1,339,711 | 5/1920 | Park | 128/16 |
| 3,592,199 | 7/1971 | Ostensen | 128/6 |
| 3,889,661 | 6/1975 | Fiore | 128/6 |
| 4,273,112 | 6/1981 | Heine et al. | 128/16 |
| 4,306,547 | 12/1981 | Lowell | 128/16 X |

FOREIGN PATENT DOCUMENTS

| | | | |
|---|---|---|---|
| 2381528 | 9/1978 | France | 128/11 |
| 375491 | 6/1932 | United Kingdom | 128/11 |
| 612116 | 11/1948 | United Kingdom | 128/11 |

Primary Examiner—George F. Lesmes
Assistant Examiner—Nancy A. B. Swisher
Attorney, Agent, or Firm—Flehr, Hohbach, Test, Albritton & Herbert

[57] ABSTRACT

A laryngoscope having a blade and separate handle containing an electrical power source is disclosed herein. A base independent of the handle is provided for the blade and includes its own bore and a light source mounted therein. The laryngoscope also includes a light guide having one end in optical communication with the light source and its opposite end disposed adjacent the opposite end of the blade for directing light from the light source at the base to the blade's opposite end. The base also includes means for disengageably mounting it to the handle in a way which places the light bulb in electrical connection with the electric power source.

35 Claims, 26 Drawing Figures

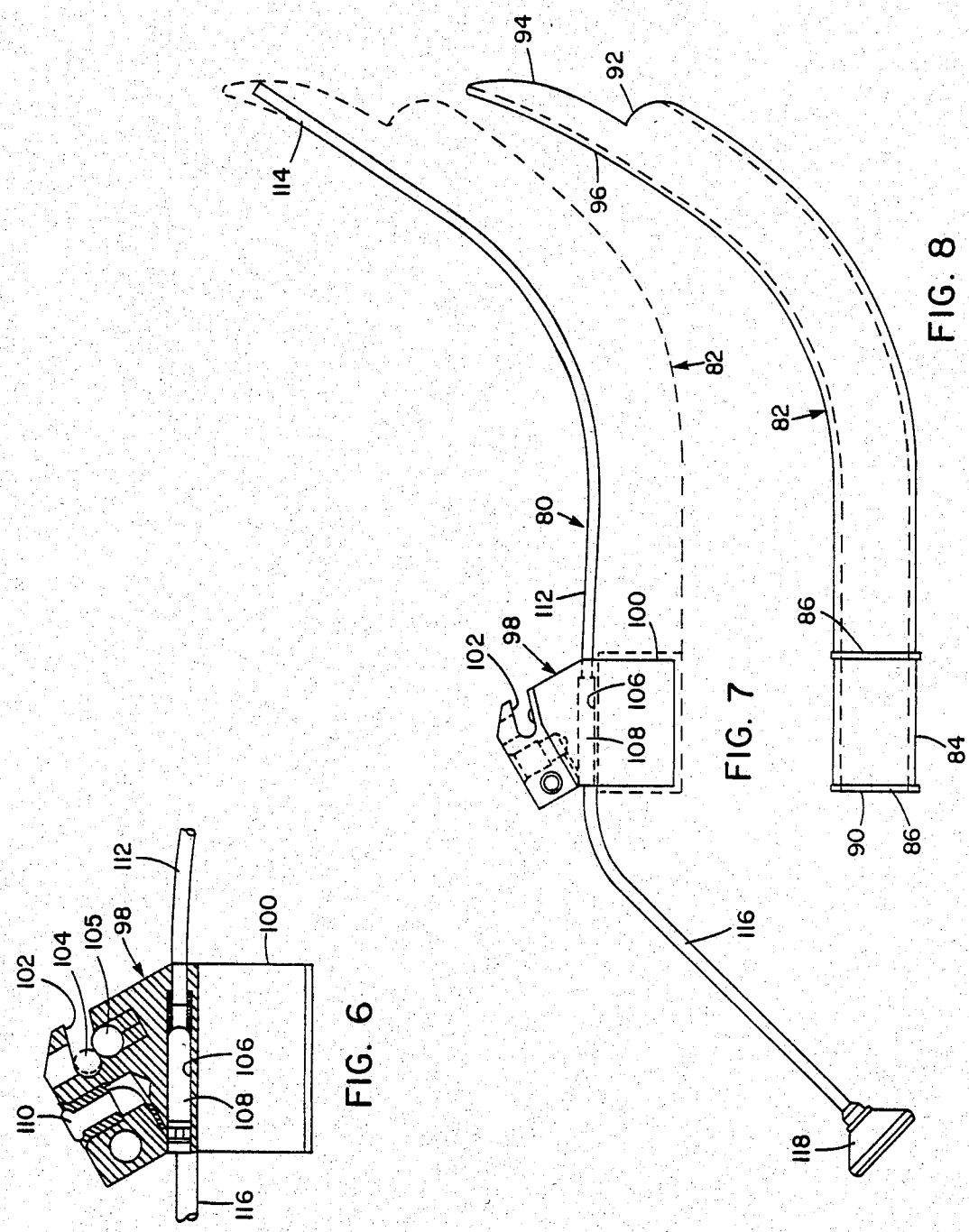

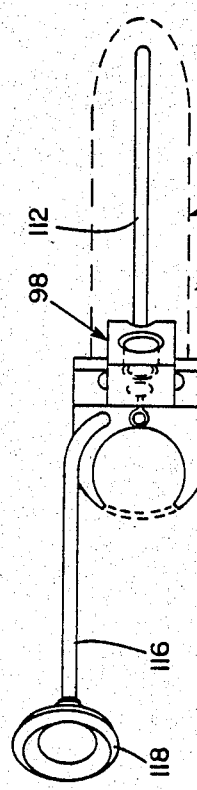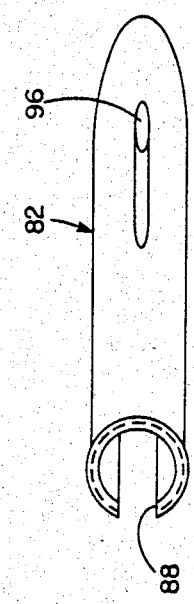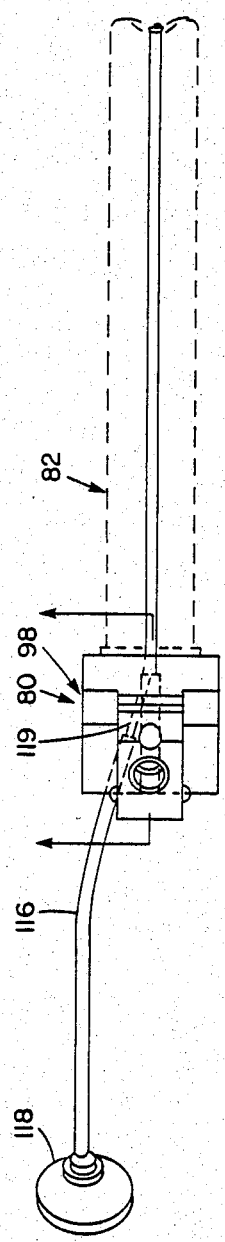

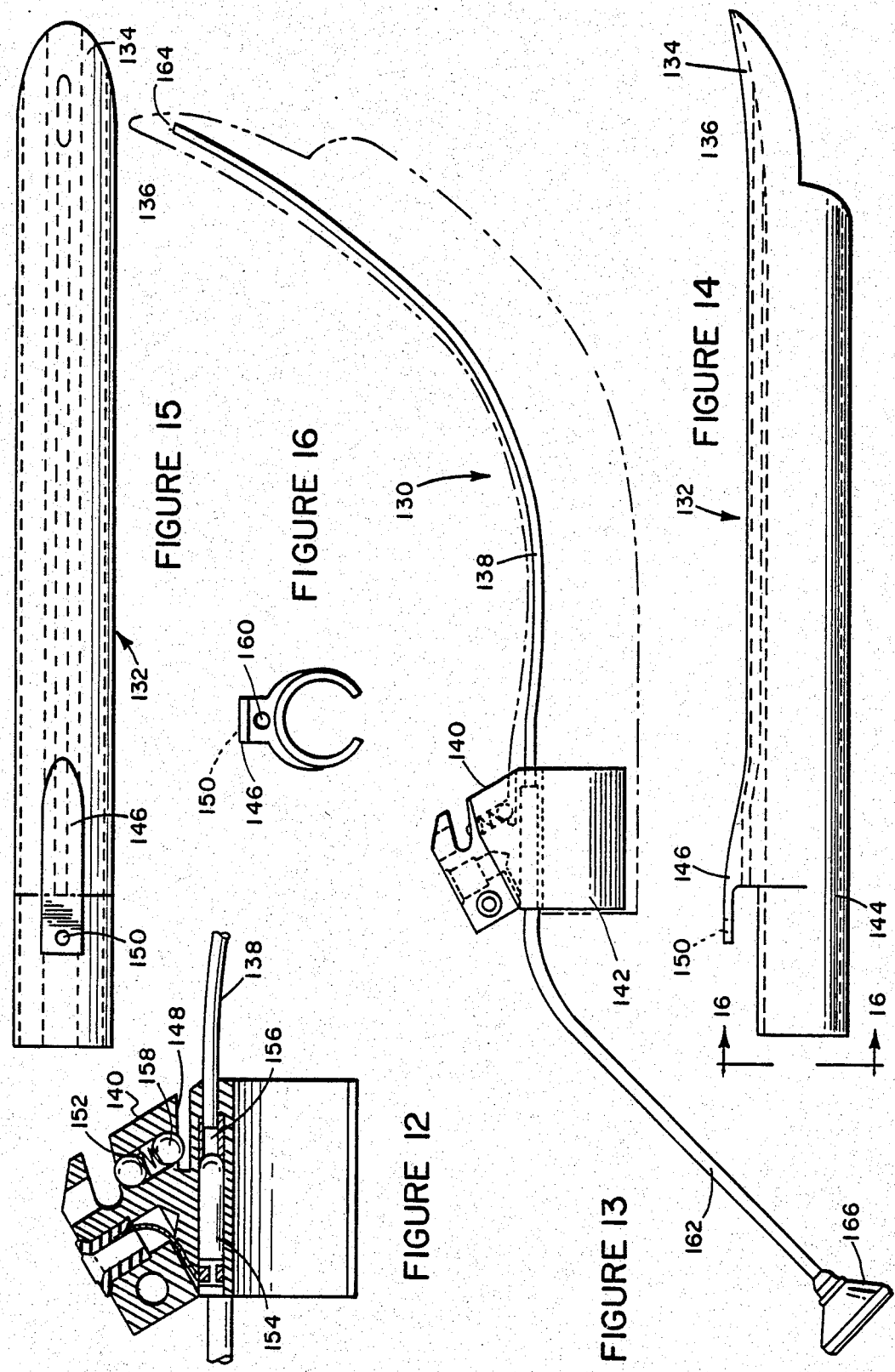

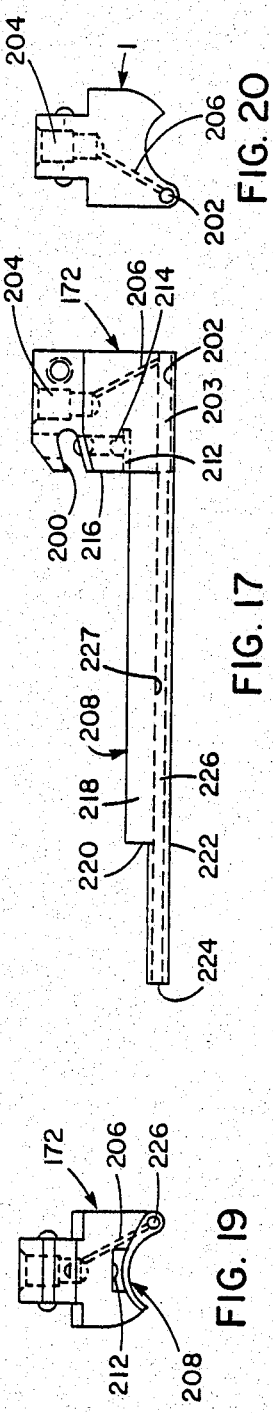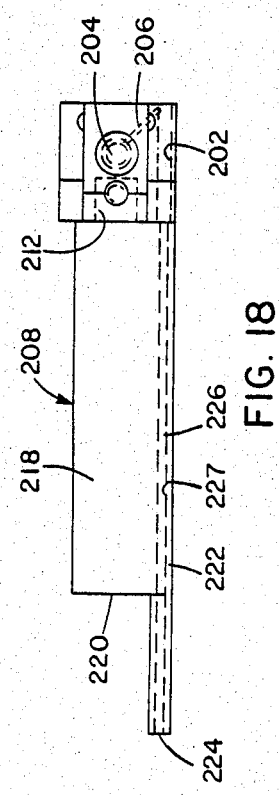
FIG. 20
FIG. 17
FIG. 18
FIG. 19

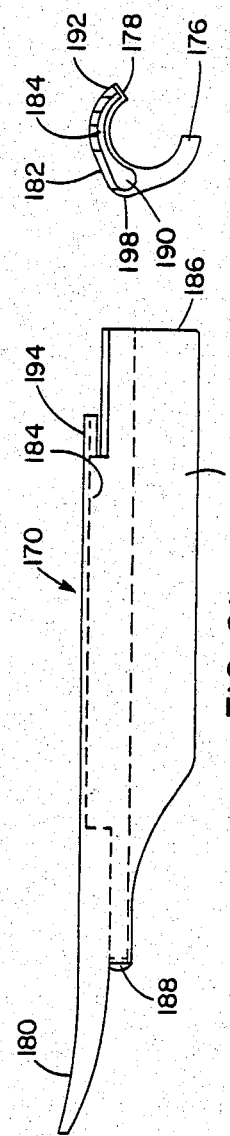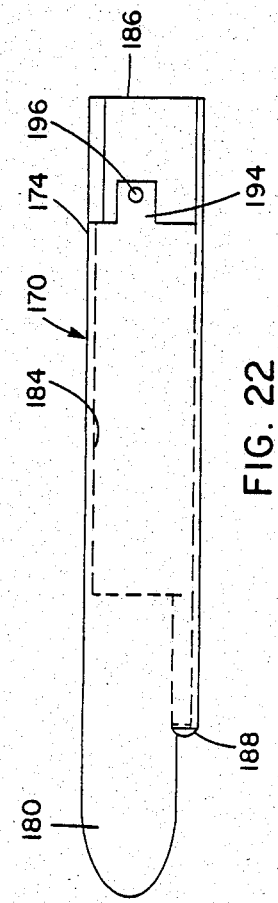

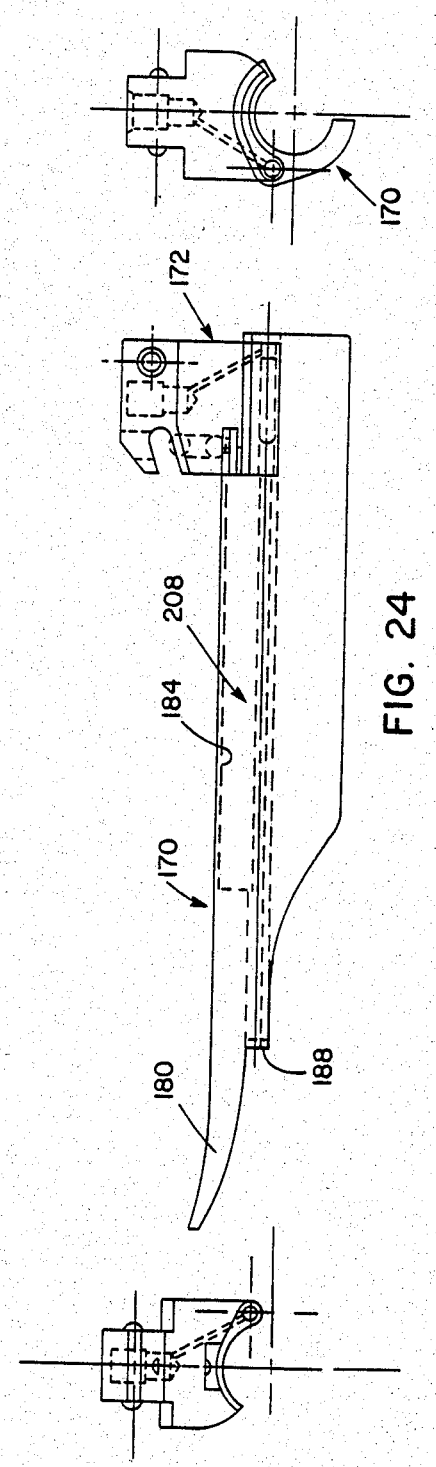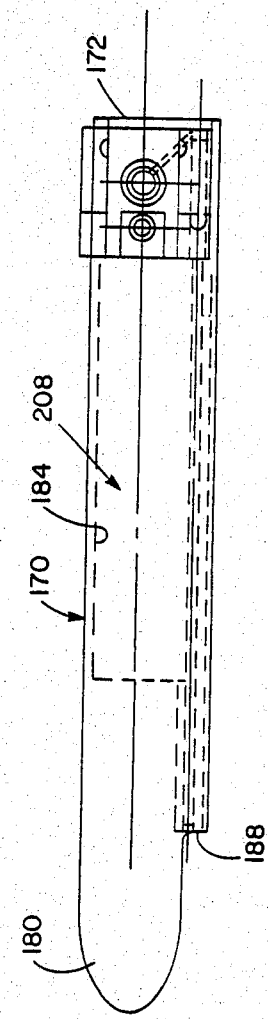

LARYNGOSCOPE WITH IMPROVED LIGHT SOURCE

This invention relates to improvements in laryngoscopes and, more particularly, to a laryngoscope whose light source is recessed in the base of the blade of the laryngoscope.

BACKGROUND OF THE INVENTION

In conventional laryngoscopes, the blade has a light bulb serving as a light source and the light bulb is located near the outer end of the blade. This light bulb is housed in a cylindrical part which projects laterally and outwardly of the outer surface of the blade, thereby adding to the maximum transverse dimension of the blade, an undesirable feature in itself. The light bulb is electrically connected by a conductor wire and by the metallic base of the blade to a battery in the handle of the laryngoscope when the handle is coupled to the base of the blade, the handle being separable from the base of the blade. The conductor wire sometimes becomes detached from the light bulb for one reason or another and this requires repair of the connection between the wire and the light bulb before the laryngoscope can be properly used again.

The wire is usually carried in a rigid conduit secured to the outer side of the blade and extending from the base along the blade to the outer end of the blade. This conduit further adds to the maximum transverse dimension of the blade. Also, the presence of moisture, such as saliva, in and around the connection between the conductor wire and the light bulb has an adverse effect on the operation of the bulb.

Because of the foregoing problems, a need has arisen for a laryngoscope with an improved light source, one which will have high reliability and will not require the need for a new design for the handle of the laryngoscope while keeping the transverse dimensions of the blade to a minimum.

SUMMARY OF THE INVENTION

The present invention satisfies the aforesaid need by providing a laryngoscope having a blade with an improved base for connection to a conventional laryngoscope handle wherein the base has a bore formed therein for housing a light bulb which, in association with a light guide extending from the bore to the outer end of the blade, serves as the light source for illuminating the region in advance of the outer end of the blade. In this way, the bulb will not present a projection at the outer end of the blade as in conventional laryngoscopes and the light guide itself conveys the light from the bulb in the base to the outer end of the blade. Thus, the outer end face of the light guide becomes the light source with respect to the region in advance of the blade.

Electrical connection between the battery and bulb is made in any suitable manner. For instance, the base can be provided with a terminal connected by a wire to the central contact of the bulb, and this terminal is placed in electrical contact with the central terminal of the battery in the handle when the handle is coupled to the base of the blade. The base and handle are of metallic material to form the other conductor between the battery and the bulb when the handle is coupled to the base. In one embodiment of the present invention, the blade is curved and the blade and base are integral with each other. The blade has a tubular configuration with a slot to guide an endotracheal tube into the trachea of a patient, the slot being provided to permit separation of the blade from the endotracheal tube after the tube has been inserted into the trachea.

In other embodiments, the blade and base are separable from each other. This permits the blade to be disposable and made sufficiently inexpensive to permit it to be thrown away after a single use. To this end, the base has a tubular connector part which releasably receives one end of the blade, the latter being of a yieldable material so that the end of the blade can be snap-fitted into place into the connector part of the base. In the alternative the connector part of the base can be yieldable and the end of the blade can be rigid. The disposable blade also has a tubular configuration and a slot for guiding an endotracheal tube into place and for permitting separation of the blade from the endotracheal tube.

With the disposable tube, a light guide is carried by the base and extends outwardly from the base and along the blade and removably through an opening near the outer end of the blade. This allows the blade to become separated from the light guide as well as the base yet the light guide can transmit light along the blade and to the outer end of the blade. A second light guide for viewing the illuminated area in advance of the blade can be provided as a separate element or can be formed with the first-mentioned light guide as a single unit.

One of the embodiments of the blade which is disposable is curved and the light guide can readily be attached to it. In another embodiment of a disposable blade, the blade is straight but can be manually bent or shaped to conform to the curvature of a curved, relatively stiff light guide. Thus, the light guide, which is stiffer than the blade, holds the blade in a curved configuration.

Additionally, any laryngoscope blade of conventional configuration can be made disposable in an analagous manner. To this, a base is provided with a lateral extension thereon. A light source is in the base and a fiber optic light guide extends distally therefrom through the extension. The extension fits into a receiving groove or channel in the blade, and is releasably held in place by a detent or other mechanism. When the blade is no longer to be used, it can be separated from the extension and be thrown away or can be washed and used again.

The primary object of this invention is to provide an improved laryngoscope in which the light source is carried in the base of the blade and the light from the light source is transmitted to the outer end of the blade by a light guide to provide increased reliability for the light source while permitting the use of the handle of a conventional laryngoscope with the base and blade.

Another object of the present invention is to provide an improved laryngoscope having a light source of the type described wherein the blade can either be integral with the base or removably mounted on the base to permit the blade to be thrown away after a single use.

Other objects of this invention will become apparent as the following specification progresses, references being had to the accompanying drawings for illustrations of the embodiments of the invention.

In the drawings:

FIG. 6 is a view similar to FIG. 1 but showing the base and attachment means for a semi-rigid, disposable laryngoscsope blade separable from the base;

FIG. 7 is a view similar to FIG. 2 but showing the disposable blade removed from the base but the blade being shown in dashed lines;

FIG. 8 is a side elevational view of the blade for releasable attachment to the base of FIG. 7;

FIG. 9 is a view similar to FIG. 3 but showing the structure of FIGS. 6-8;

FIG. 10 is an elevational view of the blade looking downwardly from above the blade of FIG. 8;

FIG. 11 is a view similar to FIG. 4 but showing the structure of FIGS. 6-8;

FIG. 12 is a view similar to FIG. 6 but showing the base for a different type of disposable blade;

FIG. 13 is a view similar to FIG. 7 but showing the base and light guide of FIG. 12;

FIG. 14 is a side elevational view of the disposable blade for use with the base of FIGS. 12 and 13;

FIG. 15 is another elevational view of the blade of FIG. 14;

FIG. 16 is an end elevational view of the blade of FIG. 14, looking in the direction of lines 16—16 of FIG. 14;

FIG. 17 is a side elevational view of another embodiment of the base of the invention, showing a transversely curved, lateral extension on the base;

FIG. 18 is a top plan view of the base and extension of FIG. 17;

FIG. 19 is an end elevational view of the base and extension of FIG. 17, looking from left to right in FIG. 17;

FIG. 20 is an end elevational view of the base of FIG. 17, looking from right to left in FIG. 17;

FIG. 21 is a side elevational view of a laryngoscope blade of conventional configuration and usable with the base and extension of FIG. 17;

FIG. 22 is a top plan view of the blade of FIG. 21;

FIG. 23 is an end elevational view of the blade of FIG. 21, looking from right to left in FIG. 21;

FIG. 24 is a view similar to FIG. 21 but showing the blade of FIG. 21 mounted on the extension of the base of FIG. 17;

FIG. 25 is a top plan view of the blade on the extension; and

FIG. 26 is an end elevational view showing the extension in the interior passage of the blade.

Figure 1:
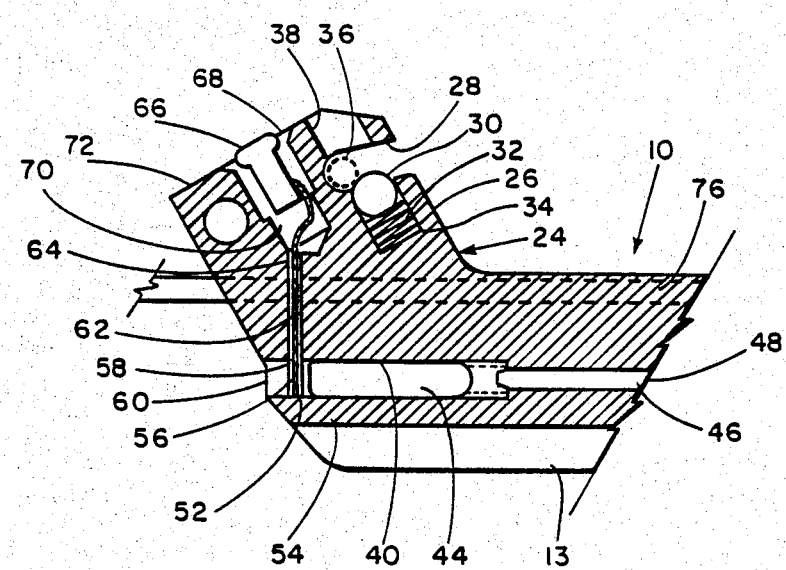
FIG. 1 is a fragmentary, cross-sectional view of a portion of an improved laryngoscope blade of the present invention, showing the light source carried by the base integral with the blade.
Figure 2:
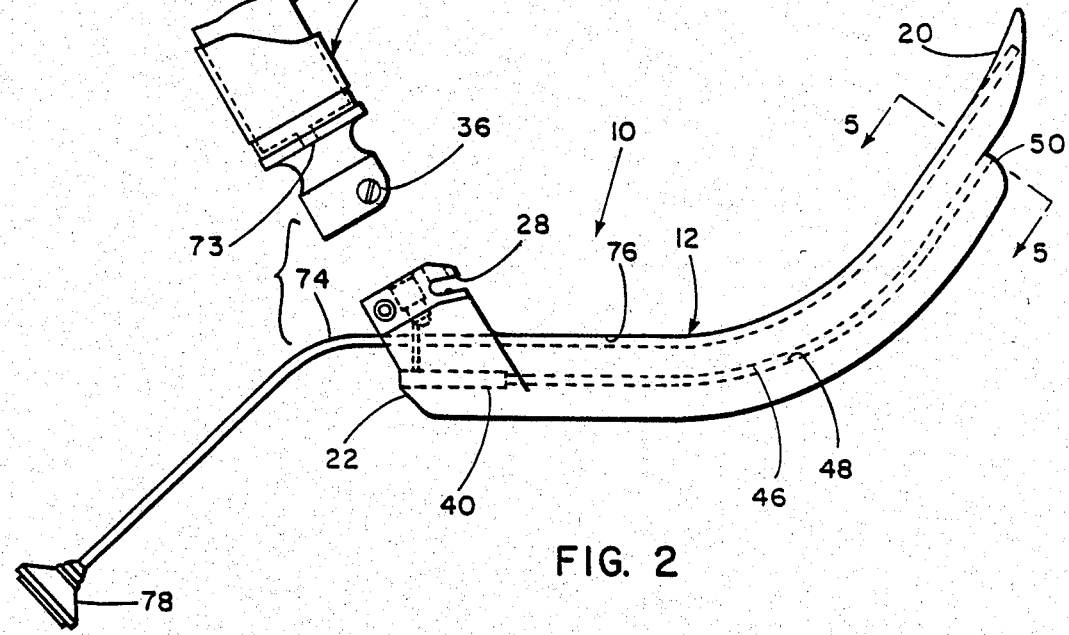
FIG. 2 is a side elevational view of the blade of this invention showing fiber optic light and visual guides in dashed lines extending along the length of the blade.
Figure 3:
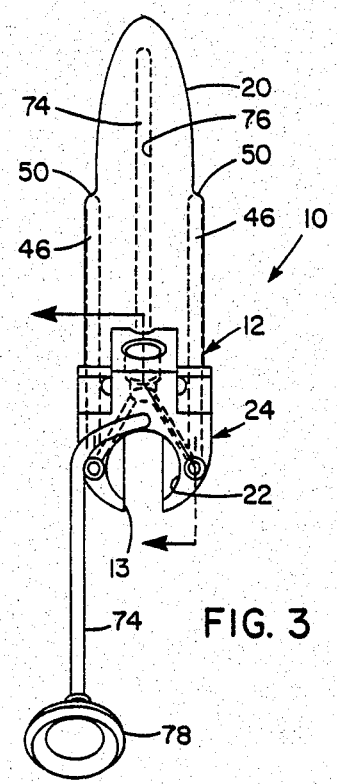
FIG. 3 is a perspective view of the laryngoscope blade of FIG. 2, looking in the direction of the end of the blade adjacent to the base thereof.

The first embodiment of the laryngoscope blade unit of the present invention is broadly denoted by the numeral 10 and is shown in FIGS. 1-4. Unit 10 includes a laryngoscope blade 12 which is curved in the manner shown in FIG. 2 and which is generally tubular and provided with slot 13 along its length in the manner shown in FIG. 5 to present a top portion 14 and a pair of sides 16 and 18. The blade is tubular throughout its entire length except for an end tip 20 which serves to elevate the epiglottis of a patient when the blade is inserted into the pharynx and larynx of the patient. The tubular and slotted nature of the blade permits an endotracheal tube (not shown) to be inserted in an open end (FIG. 2) 22 of blade 12 and to be guided along the blade so that the tube can emerge near tip 20 after the blade has been inserted into the throat of a patient. This allows the tube to enter the patient's trachea for intubation as is well known. The tube is curved to permit it to follow the conformation of the throat and to facilitate insertion of blade 12 into the throat prior to intubation. The blade could be straight, if desired. Slot 13 permits separation of the blade from the endotracheal tube when the latter is in the trachea.

Blade 12 has a base 24 adjacent to end 22 thereof, the base adapted to be coupled in a well-known manner to a conventional laryngoscope handle 25 (FIG. 2) containing a battery 27 for energizing a light source hereinafter described. To this end, base 24 has a surface 26 provided with a groove 28 therein for receiving the cross-bar 36 on the handle. A ball detent 30 in a bore 32 in the base is spring biased into groove 28 by a spring 34 so that the ball releasably holds bar 36 in place in the dashed line position of FIG. 1 to releasably connect the handle to the blade. A bore 38 is formed in base 24 to facilitate the drilling of bore 32.

Figure 5:
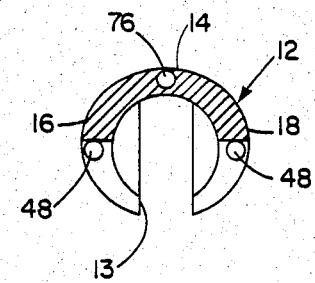
FIG. 5 is a cross-sectional view taken along line 5—5 of FIG. 2.
Figure 4:
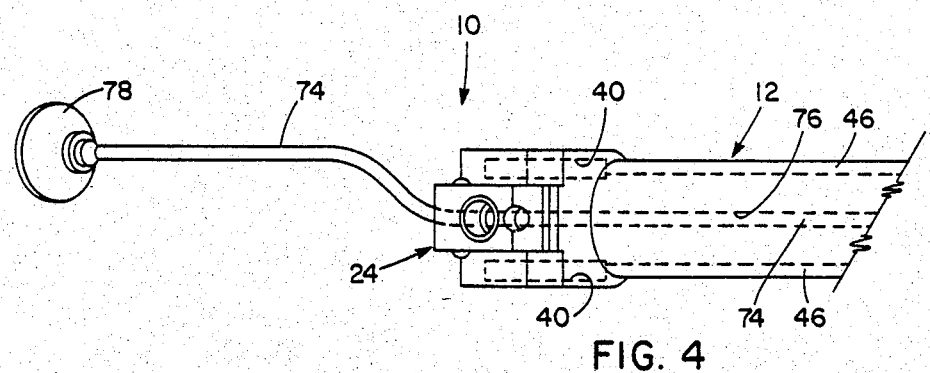
FIG. 4 is a fragmentary, perspective view of the blade looking downwardly from above the blade shown in FIG. 2.

Blade 12 has a pair of bores 40 (FIGS. 1 and 4) at the opposed sides thereof which removably receive respective light bulbs 44, only one of which is shown in FIG. 1. The light bulbs define light sources which are energized by the battery in the handle when the handle is connected to blade 12, and the light from the light sources is directed out of bores 40 through fiber optic light guides 46 which extend into and through bores 48 extending along and through the opposed sides 16 and 18 of blade 12 as is shown in FIGS. 4 and 5. The light guides terminate at end edges 50 (FIG. 2) of blade 12, and the end faces of light guides 46 define the light sources which project light forwardly of the outer end of the blade and longitudinally of tip 20 to illuminate a patient's throat area in advance of the blade when the blade is being inserted into the throat. While a pair of light sources or light bulbs 44 have been shown for purposes of illustration, it is clear that only one light bulb could be deemed necessary. The fact that light sources are in the base of the blade rather than mounted externally of the blade near edges 50 permits a compact assembly of light source and blade and eliminates electrical contact problems as well as heat that is generated in the vicinity of edges 50 when the light bulb or light source is adjacent to such edges.

Means is provided to electrically connect each light bulb 44 to the battery in the handle when the handle is coupled with the blade. For instance, each light bulb 44 is provided with a base 52 which makes electrical contact with the adjacent metallic portion 54 of base 24, and the bulb has a center terminal 56 engaged by a contact ring 58 electrically insulated from base portion 54 and held in place by an electrically threaded access cap 60 threaded into bore 40. A conductor wire 62 in electrical contact with contact ring 58 is directed through a respective bore 64 and makes electrical contact with an electrical terminal 66 press-fitted by means of a rubber grommet 68 in a second larger bore 70 extending into the end face 72 of base 24. Terminal 66 is common to the wires 62 of both bulbs 44.

When base 24 is releasably coupled to the handle with cross-bar 36 in the dashed line position of FIG. 1, terminal 66 makes electrical contact with the corresponding center terminal 73 of the battery in the handle. Moreover, bar 36, which is metallic, makes electrical contact with the bottom terminal of the battery and with base 24 so that the electrical circuit through the battery and the bulbs is completed, whereupon the bulbs are energized and the light from the bulbs passes through respective light guides 46 to their end faces near edges 50.

A fiber optic visual guide 74 extends through a bore 76 along the top of blade 12, and this visual guide extends through base 24 and outwardly therefrom. Visual guide 74 has an eyepiece 78 which permits viewing of the illuminated area in advance of the blade. Moreover, the part of light guide 74 extending outwardly from base 24 is flexible so that eyepiece 78 can be placed at various positions relative to the blade for the convenience of the user.

In use, blade 12 is releasably coupled to the handle and this causes the light bulbs to be energized immediately. Then, either while sighting through eyepiece 78 or viewing the pharynx directly through the slot in the blade, the user inserts the blade into the throat of the patient, during which time the throat area is illuminated by the light emanating from light guides 46 and the reflected light can be viewed through directly or through visual guide 74. When the blade is properly inserted in the pharynx and larynx, the endotracheal tube is guided through the tubular portion of blade 12 and into the trachea of the patient, following which the blade can then be separated from the endotracheal tube by causing the tube to pass through slot 13 of the blade while the blade is removed from the throat as the endotracheal tube remains.

FIGS. 6-11 show another embodiment of the laryngoscope blade unit of this invention in which the blade is separable from the base so that the blade can be disposed of after a single use. However, the blade need not be disposable. It can be of metallic material and be washable and capable of being sterilized.

The improved embodiment of FIGS. 6-11 is broadly denoted by the numeral 80 and includes a blade 82 of substantially the same shape and cross-section as blade 12 of unit 10 except that blade 82 has an end portion 84 provided with a pair of spaced flanges 86 which partially surround blade 82 and have ends which terminate at the slot 88 (FIG. 10) of the blade, the slot extending throughout a major portion of the blade from end 90 thereof to the opposite end margin 92 near a tip 94 provided with an opening 96 (FIG. 10).

A base 98 is used with blade 82, and base 98 has a cylindrical, slotted connector section 100 which removably receives end portion 84 of blade 82. FIG. 7 shows the blade in dashed lines in coupled relationship with section 100 with flanges 86 on the end portion 84 of the blade being adjacent to opposed ends of section 100 so as to provide a snug fit for end portion 84 and to prevent axial movement of blade 82 relative to section 100.

Base 98 is of substantially the same construction as base 24 of unit 10 (FIG. 1) except that base 98 is not integral with a blade as is base 24. This is shown in more detail in FIG. 6 wherein base 98 has a groove 102 for receiving the cross bar 104 of a handle (not shown) containing a battery, the handle being conventional in construction. A ball detent 105 is spring biased partially across groove 102 to hold bar 104 in place.

Base 98 further has a central bore 106 therethrough for containing a light bulb 108 which serves as a light source for blade unit 80. The bulb is electrically connected to a terminal 110 and to base 98 itself in the manner described above with respect to the electrical connection of bulbs 44 to a battery in a conventional handle. Thus, a description of the electrical connection of the FIG. 1 embodiment suffices for the FIG. 6 embodiment.

A fiber optic light guide 112 extends into a continuation of bore 106 to receive light from bulb 108. Light guide 112 is adapted to be removably inserted at its outer end 114 into hole 96 of blade 82 so that the outer end 114 of the light guide will terminate near tip 94 to direct light forwardly of tip 94 to illuminate the region in advance of the tip.

A fiber optic visual guide 116 has an eyepiece 118 which extends outwardly from base 98 in the opposite direction from light guide 112. Visual guide 116 has a portion 119 (FIG. 11) which merges smoothly with light guide 112 and the fibers of visual guide 116 also are embedded in light guide 112 and terminate at end face 114. Commercial fiber optic bundles are available to serve this particular purpose. Thus, light travels from light bulb 108 along light guide 112 to end face 114, whereupon reflected light from an object in advance of end face 114 is received by the fiber optic end face of visual guide 116 and the reflected light travels through visual guide 116 and eyepiece 118. In this way, only a single fiber optics guide is associated with tube 82 to minimize the structure projecting from the outer surface of the blade. While light guide 112 is shown on the back portion of blade 82, it could be at either side as well.

Laryngoscope blade unit 80 is placed in use by a first inserting the outer end of light guide 112 through hole 96 of blade 82. Then, end portion 84 of blade 82 is snap-fitted into section 100 of base 98. For this purpose, end portion 84 can be of a semi-rigid or yieldable material, such as a suitable plastic, i.e., polyethelyne or the like. The entire blade, including end portion 84, can be made of this yieldable material. In the alternative, end portion 84 can be of yieldable material and bonded to the remainder of the blade which can be of another material. Instead of a yieldable end portion 84, the latter can be rigid and section 100 on the base 98 can be of a yieldable material.

When base 98 is releasably coupled to the handle, electrical contact is made between the battery and bulb 108, causing the bulb to be activated which illuminates the area in advance of end face 114 of light guide 112. Then, the blade can be inserted into the patient's throat in the manner described above with respect to blade unit 10. Thus, the reflected light, viewed through eyepiece 118, will assist the user of unit 80 in the insertion of the blade into the throat. When the blade is properly inserted, an endotracheal tube is then directed into the open outer end of blade 82 and guided by the blade into and along the blade and eventually into the trachea of the patient. Then, the endotracheal tube and blade 82 can be separated from each other by virtue of the slot 88 in the blade so that blade 82 can be removed from the throat of the patient leaving the endotracheal tube in place.

While light bulb 108 is shown centrally of base 98 as indicated in FIG. 11, it is possible that the bulb can be at one side or the other of the base and still be operable. Preferably it is at the center so that light guide 112 can be centrally located relative to blade 82 as shown in FIG. 11.

FIGS. 12–16 show an improved version of the blade of the type which is separable from the base. The embodiment of the laryngoscope blade unit shown in FIGS. 12–16 is denoted by the numeral 130 and includes a blade 132 which is initially straight as shown in FIGS. 14 and 15, is tubular in cross-section, and is provided with a slot along its length. Blade 132 is of a flexible material, such as a suitable plastic. Its flexibility is such that it can be bent into the dashed line configuration of FIG. 13.

Blade 132 has an end tip 134 provided with a passage 136 therein and extending along the blade for receiving a curved generally rigid light guide 138 on base 140, the base having a tubular section 142 for receiving the end portion 144 blade 132. because blade 132 is of flexible material, end portion 144 can yield as it is forced into the slot of section 142. Light guide 138 has a greater stiffness than blade 132 so that, by moving the light guide through passage 136 of the blade, the blade is caused to assume the curved configuration of the light guide.

A locking tab 146 carried on the back portion of blade 132 near end portion 144 is received within a groove 148 (FIG. 12) of base 140, and a ball detent 150 removably received within a bore 152 in tab 146 releasably locks blade 132 to section 142. Base 140 has a bulb 154 received within a bore 156 in base 140 centrally of the sides of the base, and fiber optic light guide 138 extends into bore 156 and outwardly and away from base 140. A fiber optic visual guide 162 merges with fiber optic light guide 138 in the manner described above with respect to FIG. 11 of unit 80 so that only a single fiber optics guide is needed to direct light to the end face 164 of light guide 138 and to return reflected light through visual guide 162 to an eyepiece 166. Base 140 is used with a conventional laryngoscope handle in the same manner as described above with respect to unit 80.

The teachings of the present invention can be used with a laryngoscope blade of conventional construction. For instance, the blade 170 shown in FIGS. 21–23 known as a Phillips blade, can be made disposable and removably mounted on a base 172 of the type shown in FIGS. 17–20. To this end, blade 170 has a generally C-shaped body 174 which defines a pair of opposed ends 176 and 178 as shown in FIG. 23. Blade 170 is generally straight and has an outer tip 180 whose shape is shown in FIGS. 21 and 22.

Blade 170 further has an upper part 182 which is provided with a groove or passage 184 which extends from end 186 thereof to a margin 188 spaced from the outer end of tip 180. Passage 184 has a cross-sectional configuration of the type shown in FIG. 23 in which an enlarged region 190 is connected to a relatively narrow, elongated region 192. Blade 170 also has a projecting tab 194 provided with a hole 196 therein (FIG. 22). Passage 184 is transversely curved as shown in FIG. 23 and extends from one side extremity 198 of blade 170 to end 178 as shown in FIG. 23, extremity 198 being intermediate ends 176 and 178. Base 172 has a slot 200 for receiving the cross-bar (not shown) of a conventional laryngoscope handle containing a battery. The base is essentially of the same construction as base 140 of FIG. 12 in that it has a bore 202 for receiving a light bulb 203, an electrical contact terminal 204 for making contact with the battery in the handle when the handle is coupled with base 172, and a passage 206 for receiving an electrical wire for connecting the bulb in bore 202 to contact terminal 204.

Base 172 has an elongated extension 208 secured to face 210 of the base and extending outwardly therefrom as shown in FIGS. 17 and 18. Extension 208 has a cross-section of the type shown in FIG. 19 and this cross-section is complemental to groove 184 in blade 170. Thus, the extension is removably received within groove 184 by being slideable thereinto as blade 170 is coupled to base 172.

Base 172 also has a slot 212 for receiving tab 194 of blade 170 when the blade is slid onto extension 208. A ball detent 214 in a bore 216 is spring-biased into slot 212 and is adapted to enter hole 196 on tab 194 of blade 170 when the blade is in an operative position as shown in FIG. 20 for extension 208.

Extension 208 has a curved central portion 218 which terminates at end margin 220, and an enlarged portion 222 which terminates at an end margin 224. A bore 226 extends through base 172 and through enlarged side portion 222 of extension 208 and the passage terminates at margin 224. Similarly, groove 184 has its enlarged part 190 extending to margin 188 while the other part 192 of groove 184 extends to margin 189 (FIGS. 21 and 22).

A fiber optic light guide 226 is received within a bore 227 which extends through extension 208 and bore 227 communicates with bore 202. The light guide terminates near end margin 224 (FIGS. 17, 24 and 25).

In use, blade 170 is typically made of plastic so that it can be thrown away after a single use. In such a case, end margin 188 (FIGS. 21 and 22) is transparent so light from the light guide in passage 226 (FIGS. 17 and 18) will be transmitted through the face while extension 208 will be completely enclosed in the blade during use. Base 172 is coupled to a conventional laryngoscope handle to cause the bulb 203 in bore 202 to be energized, causing light from the bulb to travel along the fiber optics light guide to end 230 so that the light can then be transmitted through end face 188 and into the region near tip 180. The blade is then used in the usual manner to elevate the epiglottis of the patient so that an endotracheal tube can be inserted into the trachea of the patient. A visual guide (not shown) could be used with the assembly of FIGS. 24 and 25, if desired.

I claim:

1. In a laryngoscope having a blade and a handle containing an electrical power source: a base integral with the blade, said base being independent of the handle and having a bore therein containing an electrically actuated light bulb in its entirety, said base having first means supporting a fiber optic radiation light guide thereon at a location such that one end thereof is in optical alignment with the bore and such that the radiation guide directs radiation from the light bulb outwardly from the base through said optically aligned one end to the opposite end of the guide at a region spaced from said one end, said base having second means thereon spaced from said bore for removably coupling the base including the source to the handle, whereby the base and handle are separable from each other, and third means thereon for making electrical connection between the light bulb and the power source in the handle when the base is coupled to the handle.

2. The laryngoscope as set forth in claim 1, wherein is included means for removably retaining the bulb in the bore, said retaining means forming a part of said third means.

3. The laryngoscope as set forth in claim 1, wherein the base has a pair of opposed sides, said bulb being in a central location between the sides of the base.

4. The laryngoscope as set forth in claim 1, wherein said base has a pair of opposed sides, said bore being adjacent to one of the sides of the base.

5. The laryngoscope as set forth in claim 1, including a fiber optic visual guide carried by the base and having a first end face adjacent said opposite end of said light guide and a second end face spaced from the base and provided with an eyepiece.

6. The laryngoscope as set forth in claim 5, wherein the light and visual guides are spaced from each other.

7. The laryngoscope as set forth in claim 5, wherein a first part of the visual guide is coupled to the light guide, the remaining part of the visual guide extending outwardly from the base and merging with the light guide at a location adjacent to said base.

8. The laryngoscope as set forth in claim 7, wherein said location is interiorly of the base.

9. In a laryngoscope of the type having a blade with a separate handle attachment provided with an electrical power source: a blade adapted to be inserted into the throat of a patient to guide an endotracheal tube into the patient's trachea, said blade integral with a base at one end thereof, said base having a bore therein for receiving an electrically actuated light source in its entirety, a fiber optic light guide having a first end face in the bore for directing light from said source outwardly from the base and along said blade to a location adjacent to the opposite end of the blade, said light guide having a second end face at said opposite end of said blade, said base having means thereon for removably coupling the base to the handle; and means carried by the base for making an electrical connection between the light source and the power source on the handle when the base is coupled to the handle.

10. The laryngoscope as set forth in claim 9, wherein is included a light bulb defining said light source, said bulb being removably mounted within the bore adjacent to said first end face of the light guide.

11. The laryngoscope as set forth in claim 10, wherein is included means for removably retaining the bulb in the bore, said retaining means forming a part of said means.

12. The laryngoscope as set forth in claim 10, wherein the base has a pair of opposed sides, said bulb being in a central location between the sides of the base.

13. The laryngoscope as set forth in claim 10, wherein said base has a pair of opposed sides, said bore being adjacent to one of the sides of the base.

14. The laryngoscope as set forth in claim 9, wherein is included a visual guide coupled with the base and having a first end face adjacent to the opposite end of the blade and a second end face spaced from the base and provided with an eyepiece, said visual guide having a segment extending along said blade.

15. The laryngoscope as set forth in claim 14, wherein the light and visual guides are spaced from each other.

16. The laryngoscope as set forth in claim 14, wherein a first part of the visual guide is coupled to the light guide, the remaining part of the visual guide merging with the light guide at a location adjacent to said base.

17. The laryngoscope as set forth in claim 16, wherein said location is interiorly of the base adjacent to said bore.

18. The laryngoscope as set forth in claim 9, wherein is included a second bore and a second light source in the second bore, said connection making means being coupled to the second light source, the bores being at opposed sides of the base, and a second fiber optic light guide coupled with the second light source to direct light from the latter to said opposite end of said blade.

19. The laryngoscope as set forth in claim 9, wherein the blade has a passage therethrough in communication with said bore, said light guide being in said passage and having an end portion extending into the bore.

20. The laryngoscope as set forth in claim 19, said blade being curved and tubular and having a slot extending along the length of the blade, said slot being located to permit viewing into and through the blade to view the throat of a patient as the blade is initially inserted in the throat, said passage having the curved configuration of the blade.

21. The laryngoscope as set forth in claim 19, wherein the blade has a second passage spaced from the first passage, there being a visual guide extending through the second passage and terminating near said opposite end of the blade for viewing the region in advance of the blade.

22. The laryngoscope as set forth in claim 21, wherein is included a third passage, there being a second bore in the base with the second bore having a light bulb therein, a second light guide in the third passage and having an end portion extending into the second bore, the first and third passages being on the sides of the blade, the second passage being in the blade in a plane between the first and second passages, said blade having a slot diametrically opposed to the second passage.

23. The laryngoscope as set forth in claim 9, wherein the base and blade are integral with each other during normal operating conditions and are separable from each other for storage or maintenance purposes.

24. The laryngoscope as set forth in claim 23, wherein said connecting part is of yieldable material.

25. The laryngoscope as set forth in claim 23, wherein the blade is initially straight, said light guide being relatively stiff and the blade being relatively flexible, the blade having a passage for receiving the light guide and the blade being capable of being flexed and being shaped to the configuration of the light guide when the light guide is received in the passage.

26. The laryngoscope as set forth in claim 25, wherein the base has a tubular part for receiving an end portion of the blade when the light guide is in said passage.

27. The laryngoscope as set forth in claim 25, wherein said base has a projecting tab thereon, said base having a slot for receiving the tab when the base is coupled to the blade.

28. The laryngoscope as set forth in claim 9, wherein said blade is formed from a yieldable material, there being means on the blade for releasably retaining at least a portion of the light guide thereon.

29. The laryngoscope as set forth in claim 28, wherein the blade is curved, is tubular and has a slot extending along the length of the same, the blade having an opening therethrough near the outer end thereof, the light guide having an outer end receivable through said opening.

30. The laryngoscope as set forth in claim 28, wherein said base has a tubular connecting part, said blade having an end portion receivable in said part of the base.

31. The laryngoscope as set forth in claim 30, wherein said end portion is of yieldable material.

32. The laryngoscope as set forth in claim 31, wherein the bore is centrally disposed in the base.

33. The laryngoscope as set forth in claim 9, wherein the base has an extension extending laterally therefrom, the light guide extending through a portion of the extension, said blade having a channel for receiving the extension and the light guide.

34. The laryngoscope as set forth in claim 33, wherein the extension is transversely curved, the channel being complemental to the extension.

35. The laryngoscope as set forth in claim 33, wherein the extension is straight and extends laterally from the base.

* * * * *